(12) United States Patent
Wood et al.

(10) Patent No.: US 11,284,778 B2
(45) Date of Patent: *Mar. 29, 2022

(54) MEDICAL DEVICE POSITIONING SYSTEM

(71) Applicant: Boston Scientific Scimed, Inc., Maple Grove, MN (US)

(72) Inventors: Mark D. Wood, Shrewsbury, MA (US); Gary J. Leanna, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/737,506

(22) Filed: Jan. 8, 2020

(65) Prior Publication Data

US 2020/0138270 A1 May 7, 2020

Related U.S. Application Data

(63) Continuation of application No. 16/160,025, filed on Oct. 15, 2018, now Pat. No. 10,561,301, which is a continuation of application No. 14/498,315, filed on Sep. 26, 2014, now Pat. No. 10,136,796, which is a continuation of application No. 12/791,104, filed on
(Continued)

(51) Int. Cl.
*A61B 1/018* (2006.01)
*A61B 1/00* (2006.01)
*A61B 1/313* (2006.01)
*A61M 25/01* (2006.01)
(Continued)

(52) U.S. Cl.
CPC ........ *A61B 1/00073* (2013.01); *A61B 1/0016* (2013.01); *A61B 1/0052* (2013.01); *A61B 1/00091* (2013.01); *A61B 1/00098* (2013.01); *A61B 1/00101* (2013.01); *A61B 1/00177* (2013.01); *A61B 1/00181* (2013.01); *A61B 1/00183* (2013.01); *A61B 1/018* (2013.01); *A61B 1/2736* (2013.01); *A61B 1/313* (2013.01);
(Continued)

(58) Field of Classification Search
CPC .............. A61B 1/0008; A61B 1/00098; A61B 1/00183; A61B 1/0016
See application file for complete search history.

(56) References Cited

U.S. PATENT DOCUMENTS 3,614,891 A 10/1971 Nolte
4,176,662 A 12/1979 Frazer
(Continued)

FOREIGN PATENT DOCUMENTS

FR 2 838 325 10/2003
JP 06-319680 11/1994

*Primary Examiner* — Matthew J Kasztejna
(74) *Attorney, Agent, or Firm* — Bookoff McAndrews, PLLC (57) ABSTRACT

Embodiments of the invention include a medical device for accessing a patient's body portion and used for diagnosis and treatment of medical conditions. Embodiments of the invention may include a particular endoscopic positioning mechanism for placing an endoscope and an additional treatment device within desired body portions in order to assist in diagnosis and treatment of anatomical diseases and disorders. In particular, a medical device according to an embodiment of the invention may include an outer flexible tube and a positioning mechanism configured for rotating one portion of the flexible tube relative to another portion of the flexible tube.

20 Claims, 7 Drawing Sheets

Related U.S. Application Data

Jun. 1, 2010, now Pat. No. 8,870,754, which is a continuation of application No. 11/430,067, filed on May 9, 2006, now Pat. No. 7,753,843.

(51) Int. Cl.
*A61B 1/005* (2006.01)
*A61B 1/273* (2006.01)

(52) U.S. Cl.
CPC .... *A61M 25/0133* (2013.01); *A61M 25/0147* (2013.01)

(56) References Cited

U.S. PATENT DOCUMENTS

| | | | |
|---|---|---|---|
| 4,452,236 A | 6/1984 | Utsugi | |
| 4,699,463 A | 6/1987 | D'Amelio et al. | |
| 4,727,859 A | 3/1988 | Lia | |
| 4,779,612 A * | 10/1988 | Kishi | A61B 1/0051 600/137 |
| 4,794,911 A | 1/1989 | Okada | |
| 4,858,001 A * | 8/1989 | Milbank | A61B 1/00142 348/66 |
| 4,941,457 A | 7/1990 | Hasegawa | |
| 4,979,496 A | 12/1990 | Komi | |
| 5,312,023 A | 5/1994 | Green et al. | |
| 5,538,497 A | 7/1996 | Hori | |
| 5,624,379 A | 4/1997 | Ganz et al. | |
| 5,860,913 A | 1/1999 | Yamaya et al. | |
| 6,095,970 A | 8/2000 | Hidaka et al. | |
| 6,149,598 A | 11/2000 | Tanaka | |
| 6,190,353 B1 | 2/2001 | Makower et al. | |
| 6,354,992 B1 | 3/2002 | Kato | |
| 6,537,209 B1 | 3/2003 | Pinkhasik | |
| 6,582,357 B2 | 6/2003 | Ouchi et al. | |
| 6,605,033 B1 | 8/2003 | Uro | |
| 6,663,577 B2 | 12/2003 | Jen et al. | |
| 6,824,509 B2 | 11/2004 | Yamaya et al. | |
| 6,827,683 B2 | 12/2004 | Otawara | |
| 6,913,613 B2 | 7/2005 | Schwarz et al. | |
| 7,063,659 B2 | 6/2006 | Goto et al. | |
| 7,066,879 B2 | 6/2006 | Fowler | |
| 7,087,010 B2 | 8/2006 | Otawara et al. | |
| 7,344,494 B2 | 3/2008 | Hoeg | |
| 7,566,300 B2 | 7/2009 | Devierre | |
| 7,914,441 B2 | 3/2011 | Otawara | |
| 8,083,666 B2 | 12/2011 | Adams | |
| 8,197,400 B2 | 6/2012 | Boutillette | |
| 2003/0050639 A1 | 3/2003 | Yachia et al. | |
| 2005/0096502 A1 | 5/2005 | Khalili | |
| 2005/0131278 A1 | 6/2005 | Dickopp | |
| 2005/0272976 A1 | 12/2005 | Tanaka et al. | |
| 2006/0167342 A1 | 7/2006 | Bob et al. | |
| 2007/0055103 A1 * | 3/2007 | Hoefig | A61B 1/00179 600/173 |
| 2008/0081948 A1 | 4/2008 | Weisenburgh | |

* cited by examiner

MEDICAL DEVICE POSITIONING SYSTEM

CROSS-REFERENCE TO RELATED APPLICATIONS

This application is a continuation of U.S. application Ser. No. 16/160,025 filed on Oct. 15, 2018, which is a continuation of U.S. application Ser. No. 14/498,315, filed on Sep. 26, 2014, now U.S. Pat. No. 10,136,796, which is a continuation of U.S. application Ser. No. 12/791,104, filed on Jun. 1, 2010, now U.S. Pat. No. 8,870,754, which is a continuation of U.S. application Ser. No. 11/430,067, filed on May 9, 2006, now U.S. Pat. No. 7,753,843, all of which are incorporated herein by reference in their entireties.

FIELD OF THE INVENTION

The invention relates to an endoscope system for accessing a patient's body portion and used for diagnosis and treatment of medical conditions. For example, embodiments of the invention may include a particular endoscope positioning mechanism for placing an endoscope and an additional treatment device within desired body portions in order to assist in diagnosis and treatment of anatomical diseases and disorders.

BACKGROUND OF THE INVENTION

Endoscopes for medical use have been adopted for various diagnostic and medical treatment procedures. Endoscopes have been used for the diagnosis and treatment of a wide range of diseases and disorders that often require a physician to access the tortuous and relatively small cross-sectional areas of a patient's internal anatomical body lumens. A patient's pancreaticobiliary system (including the anatomical regions of the gall bladder, pancreas, and the biliary tree), for example, is accessed for diagnosis, and/or treatment of disorders of certain portions of the digestive system.

During treatment of the digestive system, endoscopes are often used to access and visualize a patient's pancreaticobiliary system. Once the endoscope is positioned in the desired body portion, a treatment instrument can be advanced through the working channel of the endoscope to the desired body portion. The endoscope and treatment instrument may then be manipulated as desired for visualization and treatment respectively.

Endoscopic retrograde cholangiopancreatography (ERCP) is one example of a medical procedure that uses an endoscope. ERCP enables the physician to diagnose problems in the liver, gallbladder, bile ducts, and pancreas. The liver is a large organ that, among other things, makes a liquid called bile that helps with digestion. The gallbladder is a small, pear-shaped organ that stores bile until it is needed for digestion. The bile ducts are tubes that carry bile from the liver to the gallbladder and small intestine. These ducts are sometimes called the biliary tree. The pancreas is a large gland that produces chemicals that help with digestion and hormones such as insulin.

The biliary system delivers bile produced by the liver to the duodenum where the bile assists other gastric fluids in digesting food. The biliary system includes the liver, as well as a plurality of bodily channels and organs that are disposed between the liver and the duodenum. Within the liver lobules, there are many fine "bile canals" that receive secretions from the hepatic cells. The canals of neighboring lobules unite to form larger ducts, and those converge to become the "hepatic ducts." They merge, in turn, to form the "common hepatic duct." The "common bile duct" is formed by the union of the common hepatic and the cystic ducts. It leads to the duodenum, where its exit is guarded by a sphincter muscle. This sphincter normally remains contracted until the bile is needed, so that bile collects in the common bile duct and backs up to the cystic duct. When this happens, the bile flows into the gallbladder and is stored there.

ERCP is used primarily to diagnose end treat conditions of the bile ducts, including gallstones, inflammatory strictures (scars), leaks (from trauma and surgery), and cancer. ERCP combines the use of x-rays and an endoscope. Through the endoscope, the physician can see the inside of the stomach and duodenum, and inject dyes into the ducts in the biliary tree and pancreas so they can be seen on x-rays.

An ERCP is performed primarily to identify and/or correct a problem in the bile ducts or pancreas. For example, if a gallstone is found during the exam, it can often be removed by means of a treatment instrument, eliminating the need for major surgery. If a blockage in the bile duct causes yellow jaundice or pain, it can be relieved through the use of a treatment instrument inserted through the endoscope.

Since endoscopes are often used to access the tortuous and relatively small cross-sectional areas of a patient's internal anatomical body lumens, repeated manipulation and positioning of an endoscope during a medical procedure can cause problematic side-effects. For example, repeated manipulation and positioning of the endoscope can cause unnecessary trauma to a patients internal tissues. Improper placement and repeated attempts to access a desired treatment region can exacerbate tissue trauma as well as unnecessarily prolong the medical procedure. According, there is a need for more precise endoscope manipulation as wall as manipulating an underlying treatment Instrument through an access channel of an endoscope.

Thus, it is desirable to have an endoscope assembly that can more precisely access the tortuous and relatively small cross-sectional areas of certain anatomical body lumens, and more precisely manipulate a treatment device provided within an access channel of an endoscope.

SUMMARY OF THE INVENTION

Embodiments of the present invention are directed to an improved endoscope system and a positioning device for manipulating a treatment device that obviates one or more of the limitations and disadvantages of prior medical devices.

In one embodiment, a medical device comprises an elongated flexible tube defining a longitudinal axis and including a proximal portion and a distal portion connected to the proximal portion by a joint. The flexible tube defines a lumen extending through the proximal portion and the distal portion and leading to an opening at the distal end of the flexible tube. The distal portion rotates relative to the proximal portion.

In various embodiments, the device may include one or more of following additional features: wherein the opening is disposed along an exterior side surface of the distal portion, and the lumen extends distally within the distal portion and curves to terminate at the opening; wherein the lumen is configured to receive a treatment instrument therein that can extend through the opening during a medical procedure; wherein the lumen is configured to receive a treatment instrument therein that can extend through the opening when the distal portion is rotated relative to the proximal portion; wherein the joint comprises a bearing;

wherein the joint is more flexible than both the distal and proximal portions of the flexible tube; wherein a second lumen is defined within the proximal portion and houses a torque transfer element therein; wherein a cavity is defined within the distal portion and extends distally within the distal portion, the cavity receiving a distal portion of the torque transfer element that extends distally beyond the second lumen; wherein the torque transfer element comprises a shaft extending distally to a gear arrangement in the distal portion, such that when torque is applied to the shaft, rotary motion is transferred to rotate the distal portion relative to the proximal portion; wherein rotation of the torque transfer element transmits rotary motion to the distal portion, and wherein the cavity is sized to permit rotation of the distal portion in an amount less than 360 degrees relative to the proximal portion; wherein the cavity exhibits an arc shape having a constant radius of curvature such that during rotation of the distal portion, the torque transfer element remains spaced a constant distance from a center of the elongated flexible tube; wherein stops bound the cavity to prevent rotation of the distal portion beyond a predetermined angle; wherein the lumen of the proximal portion is centrally located within the proximal portion; wherein a distal end of the lumen in the proximal portion communicates with a proximal portion of the lumen in the distal portion; wherein the lumen in the proximal portion communicates with the lumen in the distal portion through an aperture within the joint; wherein a proximal portion of the lumen of the distal portion is centrally located within the distal portion; wherein visualization and illumination components are provided within the lumen of the proximal portion and the distal portion; wherein the joint comprises a planetary gear system; wherein the planetary gear system includes a sun gear, at least one planet gear, a ring gear, and a carrier; wherein an exterior surface of the ring gear forms an exterior surface of the joint along an exterior surface of the medical device; wherein the joint is integrated with the distal portion; wherein the lumen of the flexible tube extends through an aperture provided through the planetary gear system; wherein the sun gear is grounded through connection to the proximal portion such that rotation of the carrier results in rotation of the ring gear and the distal portion; wherein the carrier is grounded through connection to the proximal portion such that rotation of the sun gear results in rotation of the ring gear and the distal portion; wherein the planetary gear system is configured to rotate the distal portion relative to the proximal portion through at least 360 degrees; wherein the joint is comprised of a helical groove provided on an interior surface of the proximal portion and an engagement pin provided on the distal portion, the engagement pin being configured for engagement with the helical groove such that forward displacement of the distal portion relative to the proximal portion results in rotation of the distal portion relative to the proximal portion; wherein the helical groove terminates at a proximal end in a linear groove provided on an interior surface of the proximal portion; wherein the linear groove terminates in an engagement section configured to releasably engage the engagement pin; wherein the engagement section comprises an interference fit connection; wherein the distal portion is configured to rotate relative to the proximal portion through at least 360 degrees; wherein rotation of the distal portion relative to the proximal portion is limited to a range of about 0-30 degrees; and wherein rotation of the distal portion relative to the proximal portion is limited to a range of about 0-20 degrees.

Another embodiment is directed to a method of positioning a treatment instrument in a body. The method comprises providing a medical device comprising: an elongated flexible tube defining a longitudinal axis and including a distal end and a proximal end, the flexible tube including a proximal portion and a distal portion connected to the proximal portion by a joint. The flexible tube defines a lumen extending through the proximal portion and the distal portion and loading to an opening at the distal end of the flexible tube. The method further includes inserting the medical device into an anatomical lumen of the body; inserting a treatment instrument through the lumen of the proximal portion and through the lumen of the distal portion; and positioning the treatment instrument by rotating the distal portion relative to the proximal portion.

In various embodiments, the method may include one or more of the following additional features: extending the treatment instrument through the lumen of the distal portion and out of the opening of the medical device into the anatomical lumen; wherein the medical device houses a shaft for transferring rotary motion to the distal portion such that when torque is applied to shaft, rotary motion is transferred to rotate the distal portion rotative to the proximal portion; retracting the treatment instrument into the medical device, repositioning the medical device within the anatomical lumen, applying torque to the shaft to rotate the distal portion, and extending the treatment instrument through the opening; wherein the treatment instrument is positioned within a bile duct during an ERCP procedure; wherein the joint comprises a bearing; wherein the distal portion is rotated 180 degrees relative to the proximal portion; wherein the opening is disposed along an exterior side surface of the distal portion, and the lumen extends distally within the distal portion and curves to terminate at the opening; wherein the joint is more flexible than both the distal and proximal portions of the flexible tube; wherein the lumen of the proximal portion is centrally located within the proximal portion; wherein a distal end of the lumen to the proximal portion communicates with a proximal portion of the lumen in the distal portion; wherein the lumen to the proximal portion communicates with the lumen to the distal portion through an aperture within the joint; whereto a proximal portion of the lumen of the distal portion is centrally located within the distal portion; wherein a second lumen is defined within the proximal portion and houses a torque transfer element therein and wherein a cavity is defined within the distal portion and extends distally within the distal portion, the cavity receiving a distal portion of the torque transfer element that extends distally beyond the second lumen; wherein rotation of the torque transfer element transmits rotary motion to the distal portion, and wherein the cavity is sized to permit rotation of the distal portion in an amount less than 360 degrees relative to the proximal portion; wherein the cavity exhibits an arc shape having a constant radius of curvature such that during rotation of the distal portion, the torque transfer element remains spaced a constant distance from a center of the elongated flexible tube; wherein stops bound the cavity to prevent rotation of the distal portion beyond a predetermined angle; wherein the joint comprises a planetary gear system including a sun gear, at least one planet gear, a ring gear, and a carrier, and wherein rotating the distal portion relative to the proximal portion comprises rotating the sun gear relative to the carrier; wherein the joint comprises a planetary gear system including a sun gear, at least one planet gear, a ring gear, and a carrier, and wherein rotating the distal portion relative to the proximal portion comprises rotating the carrier relative to the sun gear; and wherein the joint is comprised of a helical groove provided on an interior surface of the proximal portion and an engagement pin provided on the distal portion, the engagement pin being configured for engagement with the helical groove and wherein rotating the distal portion relative to the proximal portion comprises forwardly displacing the distal portion relative to the proximal portion.

Additional objects and advantages of the invention be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts. The drawing figures of this application are intended to provide a general understanding of the working elements of the underlying system. Accordingly, unless explicitly stated, the figures do not represent a literal depletion of proportional dimensions or the precise locations for the illustrated inter-related components.

According to exemplary embodiments, the invention relates to a medical device for positioning a treatment device and/or viewing a patient's internal body portion. In embodiments that use a treatment device in an endoscopic medical procedure, the treatment device can be advanced through a working channel of an endoscope, including an endoscope specifically designed and/or steed for use with the treatment device, and into a tissue tract. For purposes of this disclosure, "treatment device" or "treatment instrument" includes, for example, any wording medical device advanced through a working channel of an endoscope and for use during an endoscopic procedure. Exemplary treatment instruments include, but are not limited to, guide wires, cutting or grasping forceps, biopsy devices, snare loops, injection needles, cutting blades, scissors, retractable baskets, retrieval devices, ablation and/or electrophysiology catheters, stent placement devices, surgical stapling devices, and balloon catheters.

Figure 1:
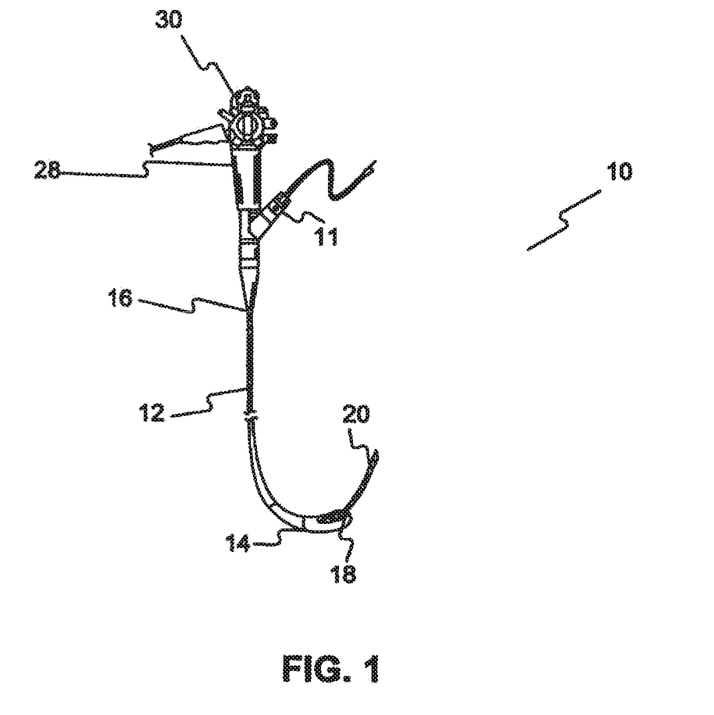
FIG. 1 is a perspective view of a prior art endoscope system.

FIG. 1 illustrates a known endoscope system. For purposes of this disclosure, "distal" refers to the end further from the device operator during use and "proximal" refers to the end closer to the device operator during use. FIG. 1 depicts an endoscope 10 including a flexible outer tube 12 extending between a distal end 14 and a proximal end 18 of the device. Endoscope 10 includes a treatment device insertion port 11 for receiving a treatment device 20 into a working channel of the endoscope 10. The distal end 14 of the endoscope system 10 includes a side facing operation window 18 that can include visualization and lighting components for viewing during a treatment procedure. In addition, a working channel (not shown) extends within the endoscope 10 and terminates at the operation window 18, thereby allowing the treatment instrument 20 to be extended from the distal end of the endoscope 10. The extension of the treatment instrument 20 at a desired treatment site can be then be viewed through the visualization components, which transmit images to the proximal end of the endoscope 10, as in known in the art. While FIG. 1 illustrates a side facing operation window 18, both front/forward facing and oblique/intermediate angled windows are known.

Figure 2:
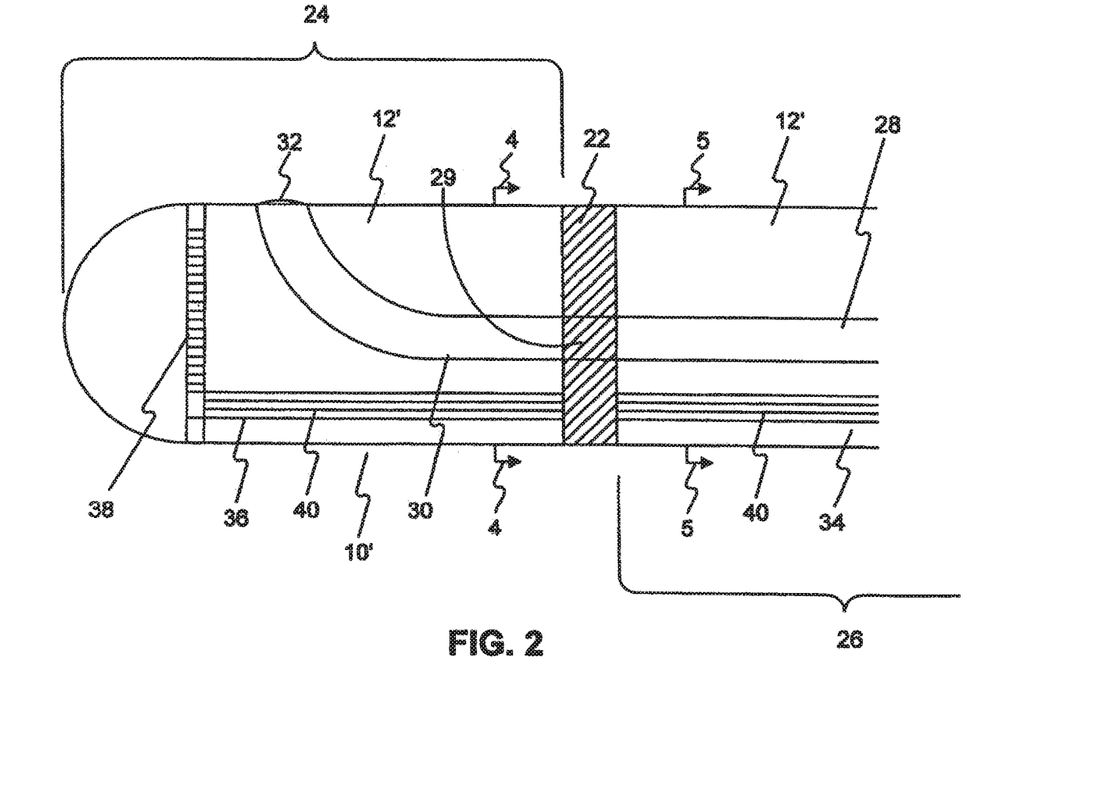
FIG. 2 is cross-sectional view of a distal portion of an endoscope according to an embodiment of the present invention.

FIG. 2 illustrates a cross-sectional view of a distal portion of an endoscope system 10' according to an exemplary embodiment. Endoscope system 10' includes an outer flexible tube 12', which extends distally from a handle (not shown) at the proximal end of the system. A joint 22 connects a rotating portion 24 of endoscope 10' to a remaining proximal portion 26 of the endoscope 10'. Joint 22, for example, can be formed of an anti-friction bearing mechanism, such as, a roller bearing, a ball bearing mechanism, or a magnetic bearing. Alternatively or additionally, joint 22 may be a portion of tube 12' that is much more flexible than the portions of tube 12' that comprise portions 24, 26 of endoscope 10'. That flexible joint 22 permits a certain degree of rotation about a longitudinal axis of endoscope 10' and tube 12' at joint 22. For example, rotation may be up to 270 degrees. In addition, joint 22 may be integrally manufactured with the other portions 24, 26 of endoscope 10' or joint 22 may be a discrete component that attaches portion 24 to portion 26. As another example, joint 22 could be comprised of an arrangement of two ring gears, one inside the other at joint 22 such that external teeth of an internal ring rear engage and transmit rotational force to internal teeth of a complementary external ring gear.

Through this arrangement (e.g., a joint between portions 24 and 26) rotating portion 24 is configured for rotation relative to proximal portion 26. That rotation is about a longitudinal axis of endoscope 10' and tube 12'. Joint 22 should be configured in a fluid-tight arrangement in order to prevent contamination and corrosion of the internal components of endoscope 10' due to contact within a patient's internal body fluids.

Other mechanisms may be used for rotating portion 24 relative to portion 26. For example, a number of pull wires wrapped around a spool could rotate portion 24. Additional examples include, but are not limited to electronic actuators, such as a stopper motor, cam drivers, a worm gear arrangement, or a pull wire system comprising a pulley type arrangement.

Although not depicted in the accompanying drawing figures, it is contemplated that the endoscope 10' may include known positioning structure for navigating the endoscope 10' and a treatment instrument through the tortuous pathways of a patient's internal body portion. For example, endoscope 10' may include pull wires for effectuating deflection during positioning and an elevator device for altering the angle at which a treatment instrument exits the endoscope 10'.

The proximal portion 26 of endoscope 10' includes a central lumen 28 within the endoscope 10', which extends from the proximal end of the endoscope 10' and terminates at the distal end of proximal portion 26. Rotating portion 24 includes a lumen 30 that connects with central lumen 28 of proximal portion 26. Lumen 30 extends distally within rotating portion 24 and curves to extend laterally, terminating at a side facing operation window 32. As seen in FIG. 2, operation window 32 is disposed along an exterior side surface of rotating portion 24. While FIG. 2 illustrates a side facing operation window 32, embodiments of the invention include both oblique/intermediate angled windows and a front/forward facing embodiment where lumen 30 extends distally to a position offset from the center of the endoscope.

Lumens 28 and 30 of endoscope 10' are configured to receive visualization components, such as, for example, known endoscopic imaging elements comprising illumination devices and fiber optic viewing elements for the transfer of images to the proximal end of the endoscope as known in the art. A portion of lumens 28 and 30 may further comprise an endoscopic working channel for receiving and guiding a treatment instrument therethrough. In such embodiments, joint 22 will include a hole 29 that connects lumens 28 and 30 during positioning of endoscope 10' and rotation of rotating portion 24 relative to proximal portion 26. In addition, a portion of operation window 32 can include a working channel exit port (see item 56 of FIGS. 6A-6B) through which a treatment instrument is extended during a medical procedure.

In some embodiments, the treatment instrument delivered through this endoscope could be designed for increased flexibility of rotation at a distal end portion, thereby accommodating rotation of the rotating portion 24 of the endoscope 10'. For example, a distal end portion of a treatment instrument could be provided with a rotatable or twistable component.

Figure 4:
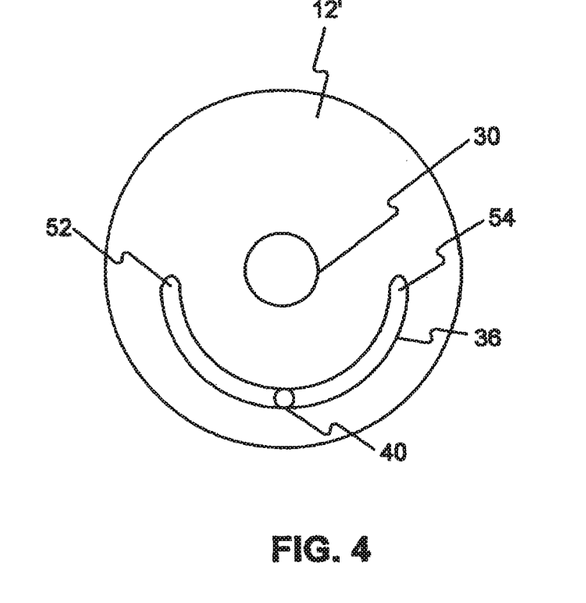
FIG. 4 is a cross-sectional view of an endoscope taken along line 4-4 in FIG. 2.
Figure 5:
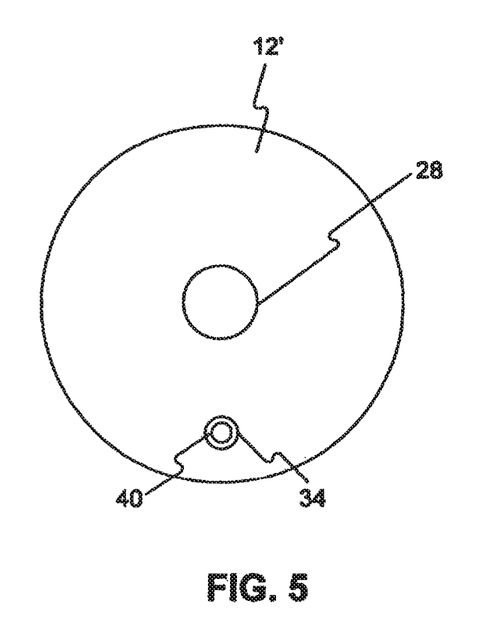
FIG. 5 is a cross-sectional view of an endoscope taken along line 5-5 in FIG. 2.

As seen in FIGS. 2, 4, and 5, proximal portion 26 includes a rotation component lumen 34 that extends distally to communicate with a rotation component cavity 36 within rotating portion 24. Just as joint 22 includes a hole 29 connecting lumens 28 and 30, joint 22 also includes an aperture (not shown) connecting lumen 34 and cavity 36. Rotation component cavity 36 extends distally within rotating portion 24 leading to a force transfer region 38.

A torque transfer element, such as, for example, flexible drive shaft 40 is provided within the rotation component lumen 34 and extends distally through cavity 36 terminating at force transfer region 38. The proximal end of drive shaft 40 is connected to any known type of positioning control mechanism at a handle at the proximal end of endoscope 10' to effectuate rotation of flexible drive shaft 40.

Figure 3:
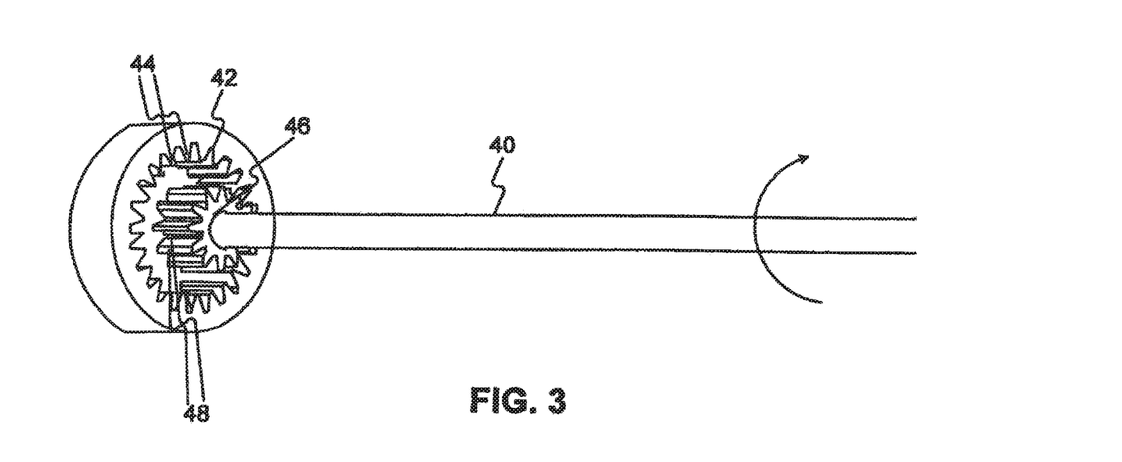
FIG. 3 is a perspective view of components of an endoscope positioning mechanism according to an embodiment of the present invention.

FIG. 3 illustrates one example of components for a torque transferring mechanism for endoscope 10'. In the example of FIG. 3, the force transferring mechanism comprises a spur gear arrangement. The arrangement includes a gear pair comprising a larger gear 42 having internal teeth 44 and a pinion 46 with external teeth 48 connected to the distal end of the flexible drive shaft 40. External teeth 48 of pinion 46 mesh with internal teeth 44 of gear 42 such that when torque is applied to flexible drive shaft 40, rotary motion is transferred to outer larger gear 42. When integrated within the endoscope system 10', the external surface of gear 42 may form part of the external surface of the outer flexible tube 12' of endoscope 10'. Alternatively, gear 42 may be embedded within tube 12'. Since gear 42 is integrated with rotating portion 24, torque applied to the flexible drive shaft 40 within rotation component lumen 34 effectuates rotation of rotating portion 24 relative to proximal portion 26. Therefore, rotation of flexible drive shaft 40 effectuates rotation of rotating portion 24 about the longitudinal axis of flexible tube 12'.

Since lumens 28 and 30 of endoscope 10' are configured to receive visualization components and at least one treatment instrument therein, complete rotation of rotating portion 24 could hinder the proper operation of those components. For example, multiple rotations of rotating portion 24 about the longitudinal axis of tube 12' could damage the internal components due to tangling of the elongated components and extreme amounts of torsion within the components housed in lumens 28 and 30. In order to avoid those possible consequences of excessive turning, permitting rotation in an amount less than a full 360 degrees is preferred. Accordingly, certain structure could be provided within the internal components of endoscope 10' in order to prevent rotation beyond a particular predetermined angular threshold.

FIGS. 4 and 5 illustrate one example of an arrangement of internal endoscope components for preventing excessive rotation of rotating portion 24. FIG. 4 represents a cross-sectional view of endoscope 10' taken along line 4-4 in FIG. 2. As seen in FIG. 4, the cross-section of rotating portion 24 depicts a portion of lumen 30 coaxially disposed therein. Rotation component cavity 36 is provided to form an arc shape within rotating portion 24. FIG. 4 also depicts the cross-section of flexible drive shaft 40, which extends through the cavity 36. FIG. 5 by contrast, depicts a cross-sectional view of endoscope 10' taken along line 5-5 in FIG. 2. FIG. 5 illustrates a portion of central lumen 28, coaxially disposed within proximal portion 26 of the endoscope 10'. In addition, FIG. 5 further depicts rotation component lumen 34, which houses flexible drive shaft 40 therein.

Arc shaped rotation component cavity 36 is formed to exhibit a constant radius of curvature. Therefore, every point along the arc shaped rotation component cavity 36 is equidistant from the center of tube 12' of endoscope 10'. Accordingly, when the flexible drive shaft 40 is rotated, first and second ends 52 and 54 of arc shaped rotation component cavity 36 provide a boundary limiting the extent to which rotating portion 24 is permitted to rotate relative to proximal portion 26. In order to prevent an excessive torque transmission or excessive torsion stored along the flexible drive shaft 10', markers, or any other type of indicia, can be provided at the positioning control mechanism to depict the allowable limits of rotation. FIG. 4 shows an exemplary angular rotation of 180 degrees. Other predetermined angular rotations permitted by cavity 36 are within the scope of the invention.

Figure 6A:
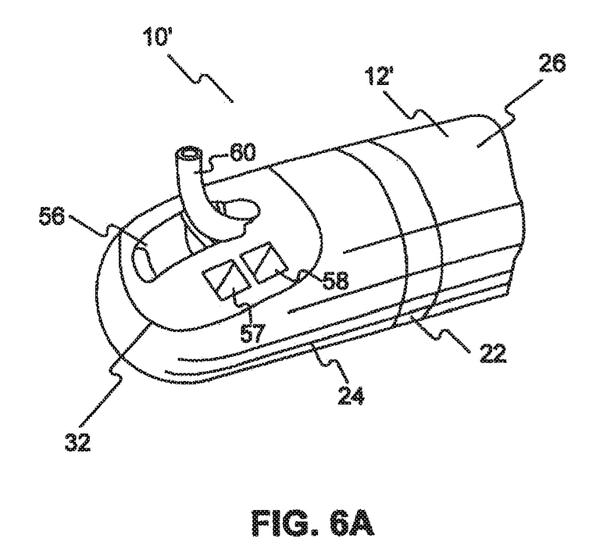
FIG. 6A is a perspective view of a distal part of an endoscope according to an embodiment of the present invention.
Figure 6B:
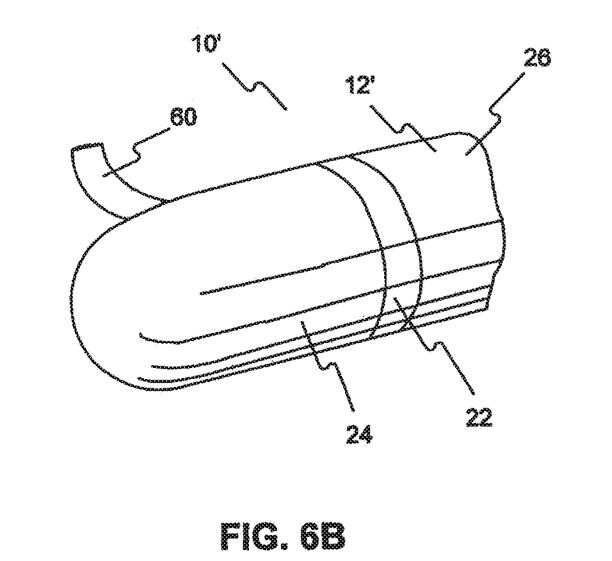
FIG. 6B is a perspective view of a distal part of an endoscope according to an embodiment of the present invention.

With reference to FIGS. 6A and 6B, rotation of rotating portion 24 is illustrated. FIG. 8A depicts rotating portion 24 including side facing operation window 32 and a working channel exit port 56 through which a treatment instrument 60 is extended. FIG. 6A also illustrates an illumination window 57 and a visualization window 58 for viewing an internal treatment site during a medical procedure as used in known endoscope devices. With reference to FIG. 6B, through actuation of flexible drive shaft 40, rotating portion 24 is rotated through a particular angle about the longitudinal axis of flexible outer tube 12'. Through this rotation, the angular orientation of exit port 56 can be precisely controlled. Accordingly, in the rotated view of FIG. 6B, neither operation window 32 nor exit port 56 are seen. This manipulation of rotating portion 24 and exit port 56 is advantageous in that precise angular rotation of exit port 56 is achieved without the unnecessary tissue trauma that may result from repeated manipulation and rotation of an entire endoscope within a patient's body portion. In addition, the arrangement of joint 22 facilitates the free rotation of portion 24 relative to proximal portion 26. Accordingly. Inefficient torque transfer and buildup of torsion along the endoscope 10' is avoided. In prior endoscope arrangements where rotation of the distal portion is effected through rotation of the entire device, improper transfer of torque from the proximal end to the distal end can lead to an unwinding, or whipping, of the distal end during placement of the endoscope. Such problems are avoided by the rotation afforded by the present system.

Figure 7:
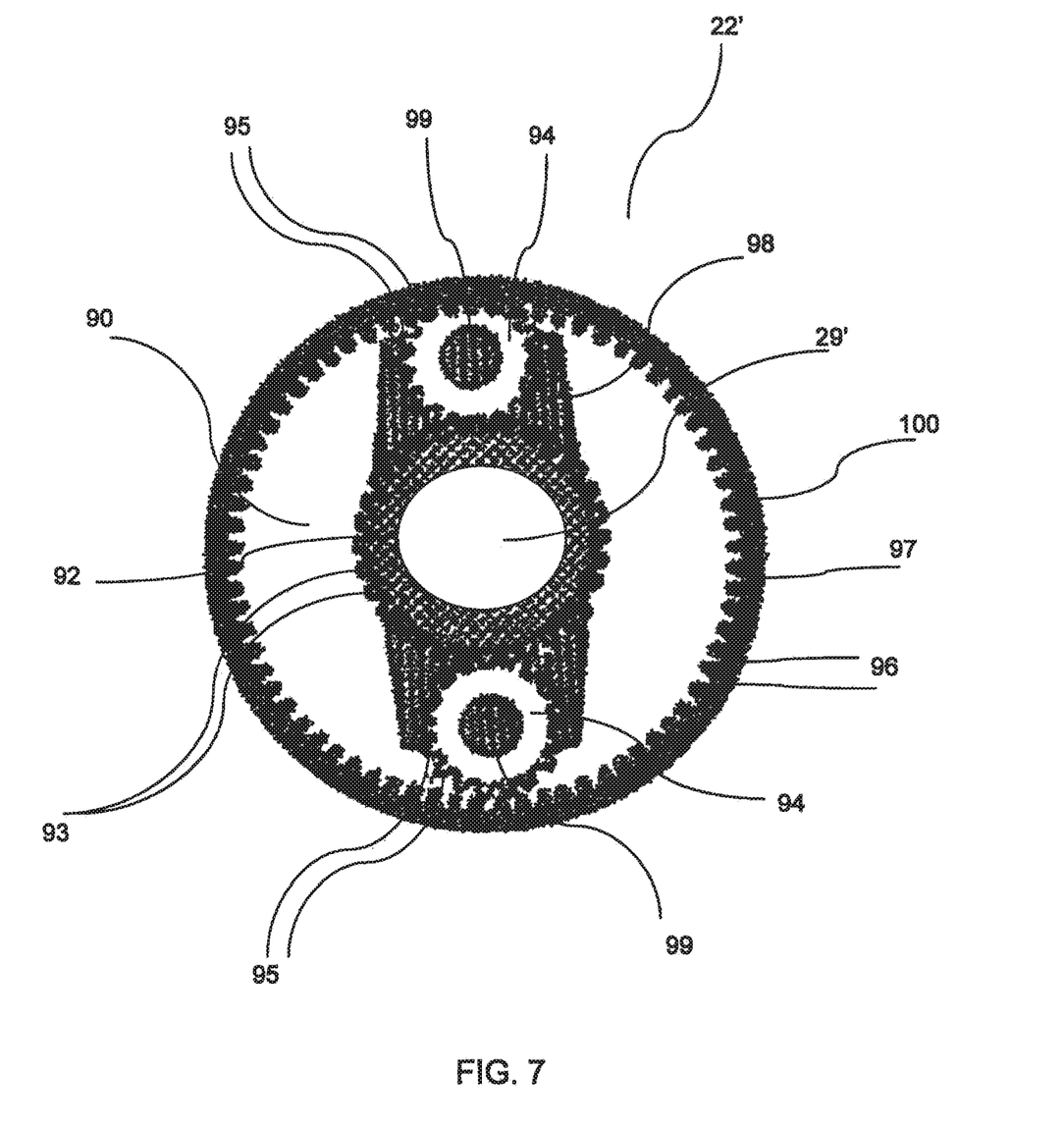
FIG. 7 illustrates a cross-sectional view of a joint in an endoscope positioning mechanism, according to another embodiment of the invention.

Other mechanisms may be used for rotating portion 24 relative to portion 26. For example, a planetary gear system can be used to permit relative rotation of two endoscope portions. FIG. 7, for example, depicts a cross-sectional view of a joint 22' including a planetary gear arrangement 90. Joint 22' is configured for use in any endoscope arrangement including a rotating portion 24 and a proximal portion 26, where rotation of a rotating portion 24 relative to a proximal portion 26 is desired (as depicted in FIGS. 6A-6B, for example). For example, an external surface 100 of joint 22' can comprise the external exposed surface of a portion of the underlying endoscope. More, particularly, the external surface 100 can be integral with, or otherwise united with, a rotating portion 24, such that rotation of external surface 100 relative to the proximal portion 26, results in rotation of rotating portion 24 relative to proximal portion 26.

In one embodiment, a central portion of the planetary gear arrangement 90 includes a central aperture 29' connecting lumens 28 and 30, as described above, during positioning of an endoscope and rotation of rotating portion 24 relative to proximal portion 26, for example. Accordingly, visualization components and at least one treatment instrument extend through aperture 29' when used in a system comprised of joint 22'.

With reference to FIG. 7, the planetary gear system includes a central cog-wheel, called the sun gear 92 having external sun gear teeth 93. The central aperture 29', described above, extends through sun gear 92. The sun gear 92 is surrounded by one or more planet gears 94. Each of the planet gears 94 include planet gear teeth 95 that engage sun gear teeth 93. The planet gears 94 also engage internal teeth 96 of an external ring gear 97, also commonly referred to as an annulus. A carrier 98 is coupled with the planet gears 93. For example, in FIG. 7, two cylindrical prongs 99 of carrier 98 are coupled with each of the illustrated planet gears 93. The central aperture 29' extends through carrier 98 just as it extends through sun gear 92.

In the planetary gear system 90, rotation is transmitted from one element to another in the gear network by grounding, also called locking, one element (i.e. either the sun gear 93, the ring gear 97, or the carrier 98) to a stationary component of structure. In an endoscope that includes joint 22' for effectuating rotation of a rotating portion 24 relative to a proximal portion 26, the locked component of planetary gear system 90 will be connected, or otherwise held stationary relative to, the proximal portion 26 of the underlying endoscope.

In one embodiment, carrier 98 is grounded by virtue of connection to a proximal portion 26 of the underlying endoscope. As such, carrier 98 will not rotate relative to the proximal portion 26. In such an arrangement, rotation of rotating portion 24 can be effectuated through rotation of sun gear 92 relative to carrier 98. For example, due to the engagement of gear teeth 93, 95, and 96, rotation of sun gear 92 in a first direction results in concurrent rotation of the planet gears 94 and, in turn, ring gear 97, in a second rotational direction opposite the first direction.

Rotation of sun gear 93 relative to carrier 98 can be effectuated through any known torque transfer element. For example, a hollow, flexible drive shaft (not shown) can be provided within the proximal portion 26 of the underlying endoscope. The proximal end of the drive shaft is then connected to any known type of positioning control mechanism at a handle at the proximal end of the underlying endoscope. Accordingly, in such an arrangement a user can control rotation of rotating portion 24 through actuation of a positioning mechanism that in turn results in rotation of sun gear 92.

In another embodiment, sun gear 92 is grounded by virtue of connection to a proximal portion 26 of the underlying endoscope. As such, sun gear 92 will not rotate relative to the proximal portion 26. In such an arrangement, rotation of rotating portion 24 can be effectuated through rotation of carrier 96 relative to sun gear 92. For example, due to the engagement of gear teeth 93, 95, and 96, rotation of carrier 98 in a first direction results in rotation of planet gears 94 about the locked sun gear 92. The movement and rotation of planet gears 94 also results in rotation of ring gear 97 in the same direction as carrier 98.

Just as described above with regard to an arrangement where sun gear 92 is rotated, rotation of carrier 98 can be effectuated through any known torque transfer element. For example, a hollow, flexible drive shaft (not shown) can be provided within the proximal portion 26 of the underlying endoscope. The proximal end of the drive shaft is then connected to any known type of positioning control mechanism at a handle at the proximal end of the underlying endoscope. Accordingly, in such an arrangement, a user can control rotation of rotating portion 24 through actuation of a positioning mechanism that in turn results in rotation of carrier 98.

Figure 8A:
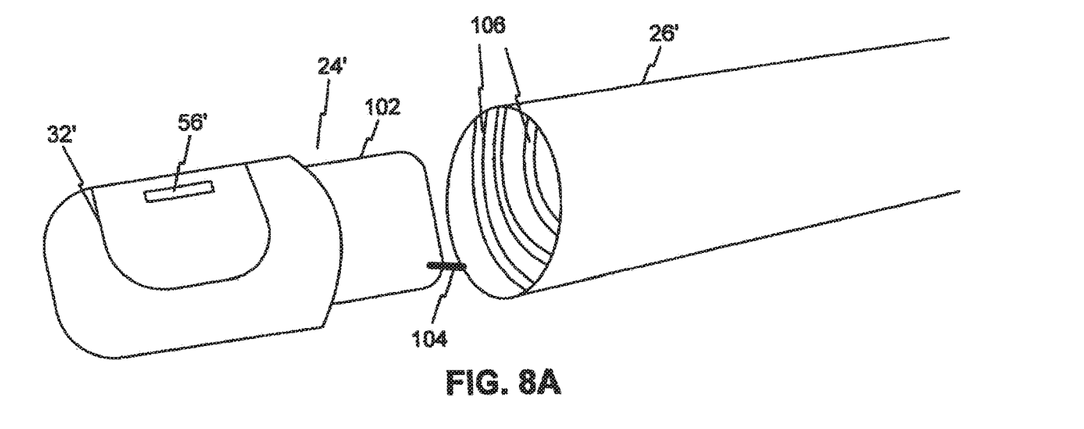
FIG. 8A depicts a partially exploded perspective view of a distal and proximal portion of an endoscope positioning mechanism, according to another embodiment of the invention.
Figure 8B:
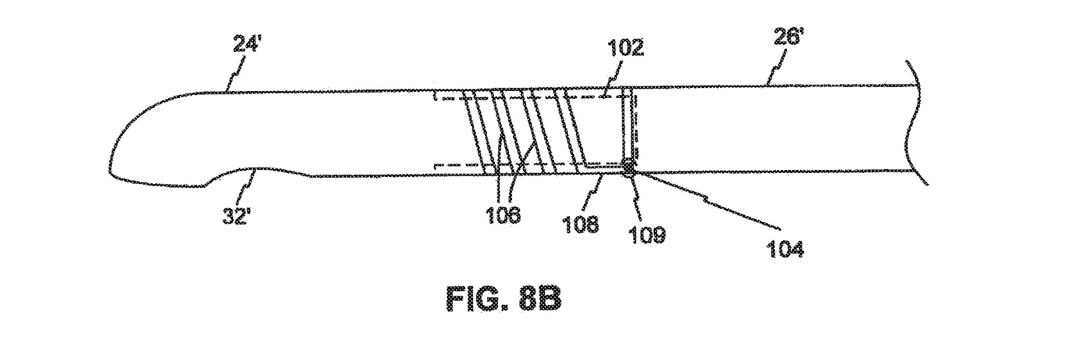
FIG. 8B deplete a side view of an assembled endoscope from FIG. 8A illustrated prior to rotation of a rotating portion.
Figure 8C:
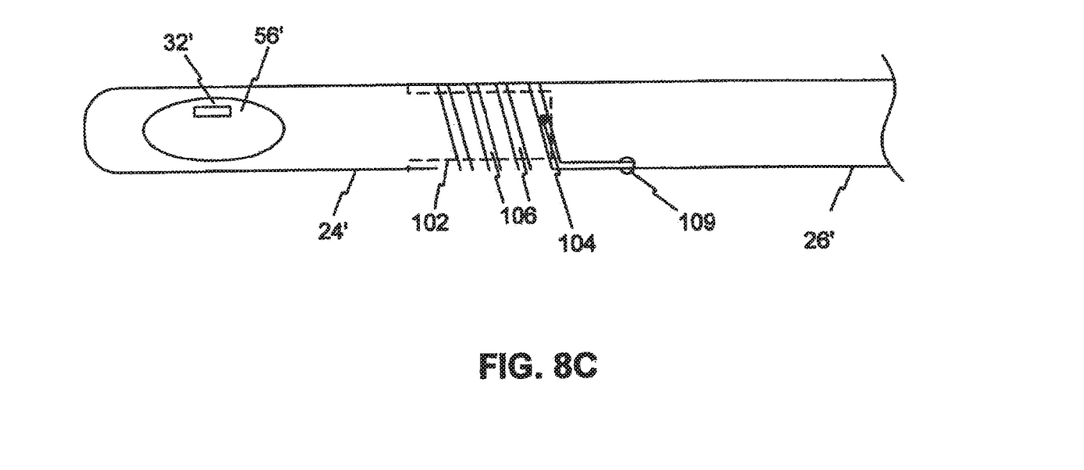
FIG. 8C deplete a side view of an assembled endoscope from FIG. 8A illustrated during rotation of a rotating portion.

FIGS. 8A-8C depict another example of a mechanism for rotating a rotating endoscope portion relative to a proximal portion. For example, a complementary pin and helical groove arrangement can be used to permit relative rotation of two endoscope portions. FIG. 8A depicts a partially exploded isometric view of two endoscope portions 24' and 26' respectively. Item 24' deplete a distal rotating portion of an underlying endoscope. Just as in the embodiment of FIGS. 6A-6B, rotating portion 24' may include an operation window 32' including a working channel exit port 56'. A proximal portion of rotating portion 24' includes a reduced diameter portion 102. The reduced diameter portion 102 may also include an engagement pin 104 outwardly radially extending therefrom.

Item 26' depicts a flexible proximal endoscope portion 26'. Proximal portion 26' can be hollow and configured for rotationally receiving the reduced diameter portion 102 within a distal portion thereof. As seen in FIGS. 8A-6C, an internal surface of proximal portion 26' may include an internal helical groove 106 extending therein. In a final configuration, the rotating portion 24' is received within the proximal portion in a fluid tight manner, but one that still allows rotation of rotating portion 24' relative to proximal portion 26'. A fluid tight arrangement can be provided through the use of sealing projections (not shown) along reduced diameter portion 102, or within the hollow proximal portion 26'. Additionally, or alternatively, a fluid tight arrangement can be provided through the use of a gasket or o-ring element.

FIG. 8B is a side view of an endoscope arrangement depleting rotating portion 24' united with proximal portion 26'. For purposes of clarity, the internal helical groove 106 of proximal portion 26' is depicted in FIG. 8B. The helical groove 106 extends proximally within proximal portion 26, transitioning into a linear groove 108. Initially, prior to rotation of rotating portion 24', engagement pin 104 of rotating portion 24' is seated within and operatively engaged within the linear groove 106 of the proximal portion 26'. In one arrangement, the very proximal end of the groove 106 terminates in a reduced size engagement section 109. Prior to rotation of rotating portion 24', the engagement pin 104 is releasably seated at the proximal end of linear groove 108 within the terminal engagement section 109.

The relation between the engagement pin 104 and engagement section 109 may be such that the pin 104 is selectively or otherwise releasable from, and in certain embodiments re-engagable with, the engagement section 109. The engagement between pin 104 and engagement section 109 may be achieved, for example, by a male/female connection in which a portion of pin 104 is inserted and received within the engagement section 109, which is of a reduced size configured to releasably receive the pin 104 by virtue of an interference fit. The engagement may be realized, for example, by a ball and socket type connection, a friction fit engagement, a screw-like configuration or any other releasable engagement mechanisms known to one having ordinary skill in the art.

Rotation of rotating portion 24' can be effectuated through controlled movement of engagement pin 104 within both linear groove 108 and helical groove 106. To initiate rotation, the rotating portion 24' must be moved relative to the proximal portion 26' with an initial forward displacement force of a magnitude great enough to overcome the force with which engagement section 109 holds pin 104. Rotating portion 24' can be displaced relative to the proximal portion 26' with any known force transfer element. Examples of suitable force transfer elements include, but are not limited to, push wires, stylets, cam drivers, stepper motors, a pull wire arrangement where a pulley type system changes a proximal pulling force into a distally directed one, and/or piezoelectric transducers provided within the proximal portion 26' of the underlying endoscope. When rotation of rotating portion 24' is desired, an operator can first linearly displace rotating portion 24' relative to proximal portion 26' such that engagement pin 104 moves along linear groove 108 and into the helical groove 106.

As seen in FIG. 8C, once rotating portion 24' is forwardly displaced such that engagement pin 104 enters helical groove 106, continued linear displacement results in rotation of rotating portion 24' relative to proximal portion 26'. FIG. 8C deplete the continued forward displacement of portion 24' resulting in controlled rotation of rotating portion 24' relative to proximal portion 26'. As seen in FIG. 8C, controlled forward displacement of engagement pin 104 results in rotation of rotating portion 24', including operation window 32'. Through the use of a force transfer element as described above, the rotating portion 24' can also be returned to the initial configuration where engagement pin 104 is re-engaged with engagement section 109.

While an arrangement comprised of an engagement pin 104 and helical groove 106 is described for effectuating rotation of rotating portion 24', other configurations are contemplated. For example, a dovetail protrusion and complementary groove could also be used. Furthermore, the helical groove 106 and pin 104 could be reversed such that a pin 104, or other protrusion, is formed on an interior of proximal portion 26' and with a helical groove formed on the reduced diameter portion 102 of rotating portion 24'.

In an alternative arrangement, the location of groove 106 and engagement pin 104 can be reversed. For example, helical groove 106 could be provided along an exterior surface of reduced diameter portion 102 of rotating portion 24' and engagement pin 104 could be provided along an internal surface of proximal portion 26'. In addition, the rotating portion 24' and proximal portion 26' could be connected and rotatable relative to each other through any type of mating thread arrangement.

In the particular embodiments of FIGS. 7-8C, rotation of one endoscope portion relative to another can be achieved in a range even greater that 360 degrees, for example. The only limiting factor in such configurations will be the extent to which internal visualization components and treatment instruments can withstand, or be enabled for, concurrent rotation within internal endoscope lumens in order to resist winding and kinking due to excessive rotation.

In all embodiments, it is to be understood that the rotation of one endoscope portion relative to another should protected from contamination by structure providing a fluid tight arrangement. In addition, the rotation of one portion relative to another can be facilitated by virtue of any lubrication element and or friction reducing structure. For example, a particular lubricious coating can be provided along the surfaces where repeated engagement or moving parts takes place.

Figure 9:
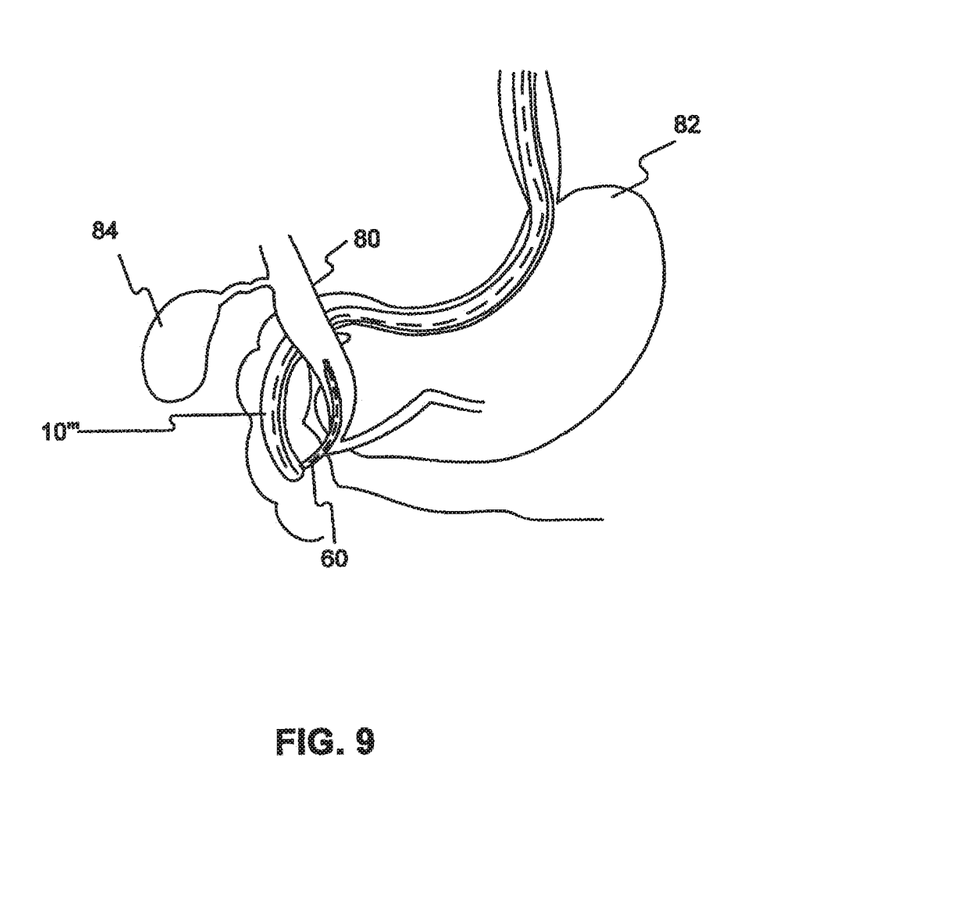
FIG. 9 illustrates the positioning of an endoscope and treatment device within a patient's body portion.

FIG. 9 illustrates the positioning of an endoscope 10' and treatment device 60 within a patient's body portion. In particular, FIG. 9 depicts the extension of a treatment instrument 60 within a particular bile duct 80 during an ERCP procedure. As seen to FIG. 9, the endoscope 10', for example, is inserted and extended through a patient's stomach 82 such that the distal end and exit port 56 (not shown) of endoscope 10' are positioned is close relation to a particular bile duct 80 leading to, for example, gall bladder 84. As seen to FIG. 8, treatment instrument 60 is extended beyond an internal working channel of endoscope 10'. The angular direction at which treatment Instrument 60 extends from endoscope 10' can then be altered, for example, by controlled rotation of rotating portion 24 relative to proximal portion 26 of endoscope 10'. Accordingly, rotation of portion 24 relative to the rest of endoscope 10' repositions the orientation of treatment instrument 60 without requiring rotation of the entire underlying endoscope 10'. Depending on the particular configuration of the underlying system, rotation of one endoscope portion relative to another can be up to 360 degrees in some embodiment (such as, for example, the embodiments of FIGS. 7 and 8A-8C). In other embodiments, excessive rotation is unnecessary. For example, in some embodiments rotation is only necessary, and the underlying structure can therefore be limited to, within a range of about 0-10 degrees, 0-20 degrees, or 0-30 degrees.

During a medical procedure, the exit port 56 along the distal portion of endoscope 10' can be repeatedly repositioned at different longitudinal locations within a patient's body. Treatment instrument 60 can then be deployed at each different location and precisely positioned to access a desired treatment site at that location. Angular adjustment of the orientation of treatment instrument 60 as it extends from endoscope 10' at consecutive treatment locations can reduce internal tissue trauma resulting from repeated rotation of an entire endoscope during a treatment procedure. Furthermore, precise manipulation of a treatment device 60 can result in shortened treatment procedures by reducing the amount of time necessary to effectuate proper position of the treatment device 60.

In addition to the above-described medical device rotation mechanisms, the incorporation of additional positioning mechanisms, including various positioning controls to effectuate bending of the flexible outer tube 12' during a medical procedure, are within the scope of this invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscopic device comprising:
    a shaft comprising a proximal section and a distal section, the distal section comprising:
        a side-facing surface including an opening; and
        a cavity extending in an arc; and
    a rotatable coupling between the proximal section and the distal section;
    wherein the cavity receives a torque transfer element moveable about a longitudinal axis of the device to drive rotation of the distal section relative to the proximal section;
    wherein the torque transfer element extends distally beyond the side-facing surface; and
    wherein the cavity has boundaries that limit rotation of the distal section relative to the proximal section to less than 360 degrees.

2. The device of claim 1, wherein the cavity limits rotation of the distal section relative to the proximal section to greater than 0 and less than or equal to 180 degrees.

3. The device of claim 1, wherein the cavity limits rotation of the distal section relative to the proximal section to greater than 0 and less than or equal to about 30 degrees.

4. The device of claim 1, wherein the device includes a lumen extending through the proximal section and the distal section, the lumen terminating at the opening.

5. The device of claim 4, wherein the device includes a handle and a port proximal to the shaft, the port being in communication with the lumen.

6. The device of claim 4, wherein the lumen extends along a central axis of the proximal section and curves laterally in the distal section to terminate at the opening.

7. The device of claim 1, wherein the distal section includes a gear rotatable relative to the torque transfer element.

8. The device of claim 1, wherein the torque transfer element comprises a flexible drive shaft.

9. An endoscopic device comprising:
    a shaft comprising a proximal section and a distal section, the distal section comprising:
        a side-facing surface including an opening;
        a lumen that terminates at the opening; and
        a cavity extending in an arc around the lumen; and
    a rotatable coupling between the proximal section and the distal section;
    wherein the cavity receives a torque transfer element moveable about a longitudinal axis of the device to drive rotation of the distal section relative to the proximal section;
    wherein the torque transfer element extends distally beyond the side-facing surface; and
    wherein the cavity has boundaries that limit rotation of the distal section relative to the proximal section to less than 360 degrees.

10. The device of claim 9, wherein the cavity limits rotation of the distal section relative to the proximal section to greater than 0 and less than or equal to 270 degrees.

11. The device of claim 9, wherein the lumen extends through the proximal section along a central axis of the shaft, and the lumen curves laterally in the distal section to terminate at the opening.

12. The device of claim 9, wherein the torque transfer element is rotatable relative to a gear incorporated in the distal section.

13. The device of claim 9, wherein a proximal end of the torque transfer element is connected to a handle of the device.

14. An endoscopic device comprising:
    a shaft comprising a proximal section and a distal section, the distal section comprising:
        a side-facing surface including an opening;
        a lumen that terminates at the opening; and
        a cavity extending in an arc with boundaries; and
    a rotatable coupling between the proximal section and the distal section;
    wherein the cavity receives a torque transfer element that transfers rotary motion to drive rotation of the distal section relative to the proximal section;
    wherein the torque transfer element extends distally beyond the side-facing surface; and
    wherein the cavity limits rotation of the distal section relative to the proximal section to greater than 0 and less than or equal to 270 degrees.

15. The device of claim 14, wherein the lumen extends through the proximal section along a central axis of the shaft, and the lumen curves laterally in the distal section to terminate at the opening.

16. The device of claim 14, wherein the cavity limits rotation to greater than 0 and less than or equal to 180 degrees.

17. The device of claim 14, wherein the device includes a port proximal to the shaft, the port being in communication with the lumen.

18. The device of claim 14, wherein a distal end of the torque transfer element is coupled to a gear.

19. The device of claim 14, wherein a proximal end of the torque transfer element is connected to a handle of the device.

20. The device of claim 14, wherein the lumen is a first lumen and the cavity is in communication with a second lumen that extends through the rotatable coupling.

* * * * *